United States Patent
Miyake et al.

(10) Patent No.: US 10,138,191 B2
(45) Date of Patent: Nov. 27, 2018

(54) 1-HALO-6,9-PENTADECADIENE AND METHOD FOR PRODUCING (7Z,10Z)-7,10-HEXADECADIENAL

(71) Applicant: SHIN-ETSU CHEMICAL CO., LTD., Tokyo (JP)

(72) Inventors: Yuki Miyake, Joetsu (JP); Takeshi Kinsho, Joetsu (JP); Tatsuya Fujii, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/951,765

(22) Filed: Apr. 12, 2018

(65) Prior Publication Data

US 2018/0305284 A1 Oct. 25, 2018

(30) Foreign Application Priority Data

Apr. 21, 2017 (JP) ................. 2017-084410

(51) Int. Cl.
| | |
|---|---|
| *C07C 45/42* | (2006.01) |
| *C07C 41/52* | (2006.01) |
| *C07C 21/00* | (2006.01) |
| *C07C 17/263* | (2006.01) |
| *C07C 21/04* | (2006.01) |

(52) U.S. Cl.
CPC .......... *C07C 45/42* (2013.01); *C07C 17/2635* (2013.01); *C07C 21/04* (2013.01); *C07C 41/52* (2013.01)

(58) Field of Classification Search
CPC .......... C07C 45/42; C07C 42/52; C07C 21/04
See application file for complete search history.

(56) References Cited

PUBLICATIONS

Heidy Herrera et. al., "Identification of a Novel Moth Sex Pheromone Component from Chilecomadia Valdiviana", J. Chem. Ecol., (2016), vol. 42, pp. 908-918.

*Primary Examiner* — Sikarl A Witherspoon
(74) *Attorney, Agent, or Firm* — Oliff PLC

(57) ABSTRACT

Provided are a 1-halo-6,9-pentadecadiene useful as an intermediate having a skipped diene skeleton and a method for producing (7Z,10Z)-7,10-hexadecadienal. More specifically, provided are a method for producing (7Z,10Z)-7,10-hexadecadienal including steps of subjecting a Grignard reagent formed from a (6Z,9Z)-1-halo-6,9-pentadecadiene to a nucleophilic substitution reaction with an orthoformate ester to obtain a (7Z,10Z)-1,1-dialkoxy-7,10-hexadecadiene; and hydrolyzing the (7Z,10Z)-1,1-dialkoxy-7,10-hexadecadiene in the absence of an oxidation reaction to obtain the (7Z,10Z)-7,10-hexadecadienal; and the like.

6 Claims, No Drawings

1-HALO-6,9-PENTADECADIENE AND METHOD FOR PRODUCING (7Z,10Z)-7,10-HEXADECADIENAL

BACKGROUND OF THE INVENTION

1. Field of the Invention

The invention relates to a 1-halo-6,9-pentadecadiene and a method for producing (7Z,10Z)-7,10-hexadecadienal.

2. Related Art

An organic compound having a skipped diene skeleton such as a structure having two double bonds bonded via a single methylene carbon, in particular, an organic compound having a Z,Z-skipped diene skeleton is abundant in natural products such as polyunsaturated fatty acids, bioactive substances and pheromones so that an intermediates having a skipped diene skeleton is very useful.

Chilean carpenter moth (*Chilecomadia valdiviana*) is known as a pest insect harmful to apples and olives and its sex pheromone is identified as (7Z,10 Z)-7,10-hexadecadienal having a Z,Z-skipped diene skeleton by Bergmann et al.

Further, Bergmann et al. have synthesized (7Z,10Z)-7,10-hexadecadienal by subjecting an aldehyde derived from 1,7-heptanediol to a Wittig reaction with a phosphorus ylide prepared from (3Z)-3-nonen-1-ol and then to deprotection and oxidation (Bergmann et al., J. Chem. Ecol. 2016, 42, 908-918).

SUMMARY OF THE INVENTION

However, the method for producing (7Z,10Z)-7,10-hexadecadienal by Bergmann et al. has difficulty in mass production on an industrial scale because the yield of the Wittig reaction is as very low as 36% and environmentally hazardous chromium is used for the oxidation reaction.

Further, when the aldehyde is synthesized through the oxidation reaction, it takes time for work-up and purification, and it is difficult to isolate the aldehyde in a high yield.

With the foregoing in view, the invention has been made. An object of the invention is to provide a 1-halo-6,9-pentadecadiene useful as an intermediate having a skipped diene skeleton and a method for producing and (7Z,10Z)-7,10-hexadecadienal.

The inventors have proceeded with an extensive investigation. As a result, it has been found that a 1-halo-6,9-pentadecadiene is a compound useful as an intermediate having a skipped diene skeleton and that (7Z,10Z)-7,10-hexadecadienal can be produced in high yield and purity by a method comprising steps of: subjecting a Grignard reagent formed from a (6Z,9Z)-1-halo-6,9-pentadecadiene to a nucleophilic substitution reaction of with an orthoformate ester to obtain a (7Z,10Z)-1,1-dialkoxy-7,10-hexadecadiene; and hydrolyzing the (7Z,10Z)-1,1-dialkoxy-7,10-hexadecadiene to obtain (7Z,10Z)-7,10-hexadecadienal in the absence of an oxidation reaction, leading to the completion of the invention.

In one aspect of the invention, there is provided a method for producing (7Z,10 Z)-7,10-hexadecadienal of Formula (9):

(9)

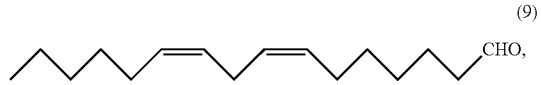

comprising steps of:
subjecting a Grignard reagent formed from a (6Z,9Z)-1-halo-6,9-pentadecadiene of Formula (1-6Z9Z):

(1-6Z9Z)

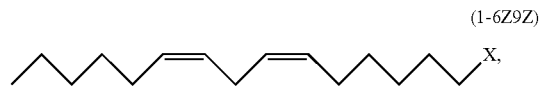

wherein X stands for a halogen atom,
to a nucleophilic substitution reaction with an orthoformate ester of Formula (2):

(2)

wherein R may be same with or different from each other and stands for an alkyl group having from 1 to 6 carbon atoms,
to obtain a (7Z,10Z)-1,1-dialkoxy-7,10-hexadecadiene of Formula (3):

(3)

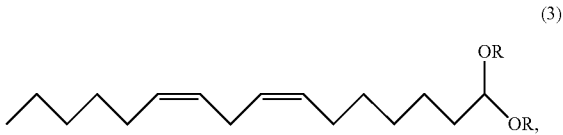

wherein R may be same with or different from each other and stands for an alkyl group having from 1 to 6 carbon atoms; and
hydrolyzing the (7Z,10Z)-1,1-dialkoxy-7,10-hexadecadiene (3) to obtain the (7Z,10Z)-7,10-hexadecadienal (9).

In another aspect of the invention, there is also provided a 1-halo-6,9-pentadecadiene of Formula (1):

$$CH_3(CH_2)_4CH=CHCH_2CH=CH(CH_2)_5X \qquad (1),$$

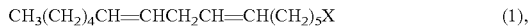

wherein X stands for a halogen atom.

In still another aspect of the invention, there is provided a method for producing a (6Z,9Z)-1-halo-6,9-pentadecadiene of Formula (1-6Z9Z), comprising a step of subjecting a triarylphosphonium (3Z)-3-nonylide of Formula (4-3Z):

(4-3Z)

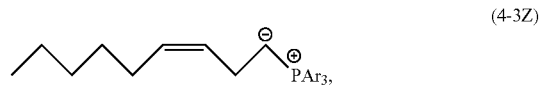

wherein Ar may be same with or different from each other and stands for an aryl group,
to a Wittig reaction with a 6-halohexanal of Formula (5):

$$OHC(CH_2)_5X \qquad (5),$$

wherein X stands for a halogen atom,
to obtain the (6Z,9Z)-1-halo-6,9-pentadecadiene (1-6Z9Z).

According to the invention, the 1-halo-6,9-pentadecadiene is useful in the production of an organic compound having a skipped diene skeleton.

Further, according to the invention, (7Z,10Z)-7,10-hexadecadienal, which is a sex pheromone of *Chilecomadia*

3

*valdiviana*, can be produced in high yield and purity in the absence of an oxidation reaction.

DETAILED DESCRIPTION OF THE PREFERRED EMBODIMENTS

First, a 1-halo-6,9-pentadecadiene of Formula (1) below, which is also usable for the production of (7Z,10Z)-7,10-hexadecadienal, will be described.

$$CH_3(CH_2)_4CH=CHCH_2CH=CH(CH_2)_5X \quad (1)$$

In Formula (1), X stands for a halogen atom and examples thereof include a chlorine atom, a bromine atom, and an iodine atom. The chlorine and bromine atoms are preferable from the standpoint of easy preparation of a Grignard reagent.

Examples of a geometric isomer of the 1-halo-6,9-pentadecadiene (I) include a (6Z,9Z)-1-halo-6,9-pentadecadiene, a (6Z,9E)-1-halo-6,9-pentadecadiene, a (6E,9Z)-1-halo-6,9-pentadecadiene, and a (6E,9E)-1-halo-6,9-pentadecadiene. From the standpoint of synthesis of (7Z,10Z)-7,10-hexadecadienal, the (6Z,9Z)-1-halo-6,9-pentadecadiene is preferable.

Examples of the (6Z,9Z)-1-halo-6,9-pentadecadiene include (6Z,9Z)-1-chloro-6,9-pentadecadiene, (6Z,9Z)-1-bromo-6,9-pentadecadiene, and (6Z,9Z)-1-iodo-6,9-pentadecadiene.

Next, a method for producing the 1-halo-6,9-pentadecadiene (1) will be described.

The 1-halo-6,9-pentadecadiene (1) may be produced by subjecting a triarylphosphonium 3-nonylide (4) to a Wittig reaction with a 6-halohexanal of Formula (5). The triarylphosphonium 3-nonylide (4) is obtained by treating, with a base, a 3-nonyltriarylphosphonium halide (4") which may be produced by reacting a 1-halo-3-nonene with a phosphorus compound. In the reaction scheme below, Ar stands for an aryl group. Although there may be a method for producing the 1-halo-6,9-pentadecadiene (1) by halogenation of 6,9-pentadecadien-1-ol, the above production method making use of a Wittig reaction is superior because the latter method has a problem in storage stability of 6,9-pentadecadien-1-ol.

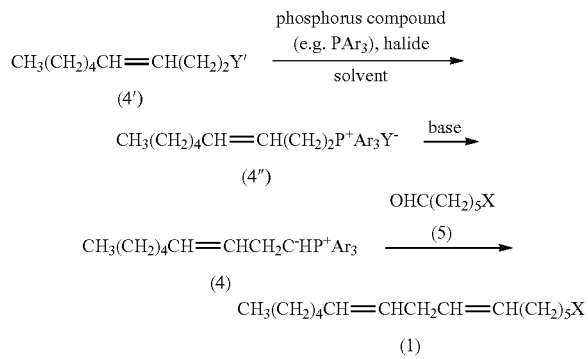

The 3-nonyltriarylphosphonium halide (4") may be obtained by reacting a 1-halo-3-nonene (4') with a phosphorus compound in a solvent and in the presence of an optional halide compound.

The 1-halo-3-nonene is expressed as Formula (4'):

$$CH_3(CH_2)_4CH=CH(CH_2)_2Y' \quad (4')$$

4

In Formula (4'), Y' stands for a halogen atom. Examples thereof include a chlorine atom, a bromine atom and an iodine atom. From the standpoint of compound stability, the chlorine atom is preferable.

Examples of a geometric isomer of the 1-halo-3-nonene (4') include a (3Z)-1-halo-3-nonene and a (3E)-1-halo-3-nonene. From the standpoint of synthesis of (7Z,10Z)-7,10-hexadecadienal, the (3Z)-1-halo-3-nonene is preferable.

Examples of the (3Z)-1-halo-3-nonene include (3Z)-1-chloro-3-nonene, (3Z)-1-bromo-3-nonene, and (3Z)-1-iodo-3-nonene.

The 1-halo-3-nonene (4') may be produced by halogenating the hydroxyl group of 3-nonen-1-ol of Formula (8).

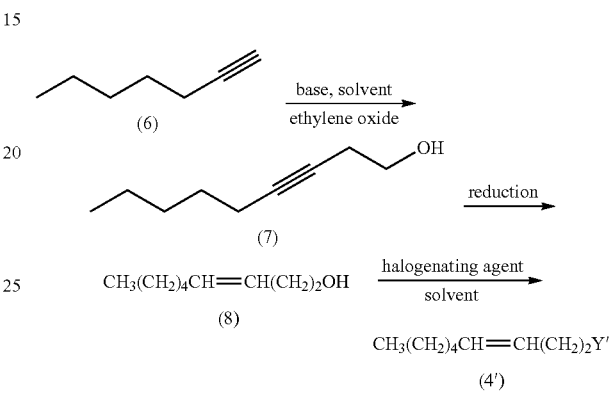

Examples of the halogenating agent include a thionyl halide such as thionyl chloride and thionyl bromide; a sulfonic halide such as methanesulfonyl chloride, p-toluenesulfonyl chloride and benzenesulfonyl chloride; a halogen such as chlorine, bromine and iodine; and a phosphorus compound such as phosphorus tribromide and phosphorus pentachloride. From the standpoint of ease of use, thionyl chloride, methanesulfonyl chloride, and p-toluenesulfonyl chloride are preferable.

The 3-nonen-1-ol (8) may be produced, for example, by reduction of the carbon-carbon triple bond of 3-nonyn-1-ol represented by Formula (7) above, which is obtained by reacting a Grignard reagent derived from 1-heptyne of Formula (6) above with ethylene oxide for extension of a carbon skeleton from the alkyne terminal end.

Examples of a method for E-selectively reducing a carbon-carbon triple bond to a carbon-carbon double bond include hydroalumination or the Birch reduction using diisobutylaluminum hydride (DIBAL) or lithium aluminum hydride (LAH).

Examples of a method for Z-selectively reducing a carbon-carbon triple bond to a carbon-carbon double bond include reduction using zinc; reduction using potassium hydroxide and N,N-dimethylformamide (DMF) in the presence of a palladium catalyst such as palladium acetate; and a hydrogenation reaction using a nickel catalyst such as nickel boride, a Lindlar's catalyst, a palladium catalyst such as palladium hydroxide or palladium carbon, or a platinum catalyst.

Examples of the phosphorus compound to be used for preparation of the 3-nonyltriarylphosphonium halide (4") include a triarylphosphine compound such as triphenylphosphine and tritolylphosphine. From the standpoint of reactivity, triphenylphosphine is preferable.

The amount of the phosphorus compound to be used for preparation of the 3-nonyltriarylphosphonium halide (4") is preferably from 1.0 to 2.0 mol per mol of the 1-halo-3-nonene (4') from the standpoint of reactivity.

Examples of the halide to be used for preparation of the 3-nonyltriarylphosphonium halide (4") include sodium iodide, potassium iodide, sodium bromide, and potassium bromide. From the standpoint of reactivity, iodides such as sodium iodide and potassium iodide are preferable. The halide may be used singly or in combination of two or more. Although addition of the halide is optional, addition of an iodide such as sodium iodide or potassium iodide as the halide is preferable from the standpoint of reactivity. It is because the reaction between 1-chloro-3-nonene or 1-bromo-3-nonene and a phosphorous compound proceeds at a markedly low reaction rate, differing from a conventional reaction between an alkyl halide and a phosphorus compound.

The amount of the halide to be used for preparation of the 3-nonyltriarylphosphonium halide (4") is preferably from 0.1 to 2.5 mol per mol of the 1-halo-3-nonene (4') from the standpoint of reactivity.

In Formula (4"), Y stands for a halogen atom and examples thereof include a chlorine atom, a bromine atom, and an iodine atom. When the 3-nonyltriarylphosphonium halide (4") is prepared in the absence of the halide, Y is the same halogen atom as Y'. When it is prepared in the presence of an iodide as the halide, Y is the same halogen atom as Y', or an iodine atom.

In Formula (4"), Ar stands for an aryl group.

The reaction temperature for preparation of the 3-nonyltriarylphosphonium halide (4") is preferably from 60 to 180° C., though an optimum temperature differs depending on a solvent used.

The reaction time for preparation of the 3-nonyltriarylphosphonium halide (4") is preferably from 5 to 25 hours, though it differs depending on a solvent used or a reaction scale.

The triarylphosphonium 3-nonylide (4) may be obtained by adding a base to the obtained 3-nonyltriarylphosphonium halide (4") in a solvent. The 3-nonyltriarylphosphonium halide (4") may be converted directly into the triarylphosphonium 3-nonylide (4) by adding a base to the reaction product mixture of the 3-nonyltriarylphosphonium halide (4"). Alternatively, the isolated 3-nonyltriarylphosphonium halide (4") may be converted into the triarylphosphonium 3-nonylide (4) by adding a solvent and a base. The triarylphosphonium 3-nonylide (4) is expressed as Formula (4):

$$CH_3(CH_2)_4CH=CHCH_2C^-HP^+Ar_3 \quad (4)$$

In Formula (4), Ar may be same with or different from each other and stands for an aryl group. The aryl group preferably has from 6 to 7 carbon atoms.

Examples of the aryl group include a phenyl group and a tolyl group. From the standpoint of ease of synthesis, a phenyl group is preferable, and more preferably each of the three aryl groups is a phenyl group.

Examples of a base to be used for preparation of the triarylphosphonium 3-nonylide (4) include an alkyl lithium such as n-butyl lithium and tert-butyl lithium; a metal alkoxide such as potassium tert-butoxide, sodium tert-butoxide, potassium methoxide, sodium methoxide, potassium ethoxide and sodium ethoxide; and a metal amide such as lithium diisopropylamide and sodium bis(trimethylsilyl)amide. From the standpoint of reactivity, the base is preferably the metal alkoxide, more preferably potassium tert-butoxide, sodium methoxide or sodium ethoxide.

The amount of the base to be used for preparation of the triarylphosphonium 3-nonylide (4) is preferably from 0.8 to 2.0 mol per mol of the 1-halo-3-nonene (4') from the standpoint of reactivity.

The reaction temperature for preparation of the triarylphosphonium 3-nonylide (4) is preferably from −78 to 25° C., though an optimum temperature differs depending on a solvent or base to be used.

The reaction time for preparation of the triarylphosphonium 3-nonylide (4) is preferably from 0.5 to 6 hours, though it differs depending on a solvent used or a reaction scale.

Since the 1-halo-3-nonene (4') is a homoaryl halide, 1,3-nonadiene, which is a terminal diene, may be formed as a by-product as a result of an elimination reaction in the step of adding the base to the 3-nonyltriarylphosphonium halide (4") to prepare the triarylphosphonium 3-nonylide (4). In fact, when potassium tert-butoxide was reacted as a base at −10° C. for preparation of the triarylphosphonium 3-nonylide (4), the triarylphosphonium 3-nonylide (4) was not obtained, but 1,3-nonadiene, which is a terminal diene obtained by decomposition of a phosphonium salt of the 1-halo-3-nonene (4'), was obtained. In order to suppress said elimination reaction, when potassium tert-butoxide is used as a base, the reaction temperature for preparation of the triarylphosphonium 3-nonylide (4) is preferably from −78 to −30° C., more preferably from −78 to −40° C.

It has been found that when a metal alkoxide of an alcohol having a pKa of from 12.0 to 16.5 is used as a base, the elimination reaction can be suppressed even the reaction temperature for preparation of the triarylphosphonium 3-nonylide (4) is from −20 to 0° C.

The pKa of the alcohol corresponding to the metal alkoxide is preferably from 12.0 to 16.5, more preferably from 15.0 to 16.5 from the standpoint of preparation of a phosphorus ylide and suppression of the elimination reaction. The term "pKa" as used herein means a value of the pKa when water is used as a solvent.

Examples of the metal alkoxide of an alcohol having a pKa of from 12.0 to 16.5 include a sodium or and potassium salt of an aliphatic alcohol having from 1 to 6 carbon atoms such as methanol (pKa: 15.5), ethanol (pKa: 15.9), propanol (pKa: 16.1), 2-propanol (pKa: 16.5) and n-butanol (pKa: 16.1), or a haloalcohol such as 2,2,2-trifluoroethanol (pKa: 12.5).

When the metal alkoxide of an alcohol having a pKa of from 12.0 to 16.5 is used as the base, the reaction temperature for preparation of the triarylphosphonium 3-nonylide (4) may be preferably as low as from −78 to −30° C., or may be a higher temperature, preferably from −20 to 0° C., more preferably from −10 to 0° C.

Examples of a solvent to be used for preparation of the 3-nonyltriarylphosphonium halide (4") and the triarylphosphonium 3-nonylide (4) include hydrocarbons such as toluene, xylene and hexane; ethers such as tetrahydrofuran and diethyl ether; and polar solvents such as N,N-dimethylformamide, N,N-dimethylacetamide and acetonitrile. From the standpoint of reactivity, ethers such as tetrahydrofuran and polar solvents such as acetonitrile and N,N-dimethylacetamide are preferable. The solvent may be used singly or in combination of two or more. The amount of the solvent is preferably from 300 to 2000 g per mol of the 1-halo-3-nonene (4') from the standpoint of reactivity.

A 6-halohexanal to be subjected to a Wittig reaction with the obtained triarylphosphonium 3-nonylide (4) is expressed as Formula (5):

OHC(CH$_2$)$_4$CH$_2$X                        (5)

In Formula (5), X stands for a halogen atom and examples thereof include a chlorine atom, a bromine atom, and an iodine atom. From the standpoint of compound stability, a chlorine atom is preferable.

From the standpoint of synthesis of the (7Z,10Z)-7,10-hexadecadienal, 6-chlorohexanal and 6-bromohexanal are preferable.

The reaction temperature for the Wittig reaction is preferably from −78 to 25° C., though an optimum temperature differs depending on a solvent used. When the Wittig reaction is carried out Z-selectively, the reaction temperature is preferably from −78 to 10° C. When the Wittig reaction is carried out E-selectively, a reaction at from −78 to −40° C. is preferably followed by a reaction in the conditions of the Schlosser modification or the like in which the intermediate thus obtained is treated with a strong base such as phenyl lithium.

The reaction time for the Wittig reaction is preferably from 0 to 5 hours, though it differs depending on a reaction scale.

The kind and amount of the solvent for the Wittig reaction may be the same as or different from the kind and amount of solvent to be used for preparation of the phosphonium salt and phosphorus ylide of the 1-halo-3-nonene (4').

From the standpoint of synthesis of the (7Z,10Z)-7,10-hexadecadienal, the later-mentioned (6Z,9Z)-1-halo-6,9-pentadecadiene of Formula (1-6Z9Z) is obtained preferably by subjecting the 6-halohexanal of Formula (5) above to a Wittig reaction with a triarylphosphonium (3Z)-3-nonylide of Formula (4-3Z) below. In Formula (4-3Z), Ar may be same with or different from each other and stands for an aryl group. The aryl group preferably has from 6 to 7 carbon atoms. Examples of the aryl group include a phenyl group and a tolyl group. From the standpoint of ease of synthesis, a phenyl group is preferable, and more preferably each of the three aryl groups is a phenyl group.

(4-3Z)

Next, a method for producing a (7Z,10Z)-1,1-dialkoxy-7,10-hexadecadiene (3) will be described.

The (7Z,10Z)-1,1-dialkoxy-7,10-hexadecadiene of Formula (3) below may be produced by converting the (6Z,9Z)-1-halo-6,9-pentadecadiene of Formula (1-6Z9Z) into a corresponding Grignard reagent and then subjecting the Grignard reagent to a nucleophilic substitution reaction with an orthoformate ester (2).

(1-6Z9Z) 1) Mg
2) orthoformate(2)

(3)

The Grignard reagent from the (6Z,9Z)-1-halo-6,9-pentadecadiene (1-6Z9Z) may be prepared by reacting the (6Z,9Z)-1-halo-6,9-pentadecadiene (1-6Z9Z) with magnesium in a solvent.

The amount of magnesium to be used for preparation of the Grignard reagent from the (6Z,9Z)-1-halo-6,9-pentadecadiene (1-6Z9Z) is preferably from 1.0 to 2.0 mol per mole of the (6Z,9Z)-1-halo-6,9-pentadecadiene (1-6Z9Z).

Examples of the solvent to be used for preparation of the Grignard reagent from the (6Z,9Z)-1-halo-6,9-pentadecadiene (1-6Z9Z) include hydrocarbons such as toluene and hexane; and ethers such as tetrahydrofuran and diethyl ether. From the standpoint of the reaction rate for the formation of the Grignard reagent, tetrahydrofuran is preferable. The amount of the solvent is preferably from 100 to 600 g per mol of the (6Z,9Z)-1-halo-6,9-pentadecadiene (1-6Z9Z) from the standpoint of reactivity.

The reaction temperature for preparation of the Grignard reagent from the (6Z,9Z)-1-halo-6,9-pentadecadiene (1-6Z9Z) is from 30 to 120° C., though it differs depending on the solvent used.

The reaction time for preparation of the Grignard reagent from the (6Z,9Z)-1-halo-6,9-pentadecadiene (1-6Z9Z) is preferably from 1 to 30 hours, though it differs depending on the solvent used or a reaction scale.

The orthoformate ester is expressed as Formula (2):

$$H-\underset{\underset{OR}{|}}{\overset{\overset{OR}{|}}{C}}-OR \qquad (2)$$

In Formula (2), R may be same with or different from each other and stands for an alkyl group having from 1 to 6 carbon atoms, preferably from 1 to 3 carbon atoms, and examples thereof include a methyl group, an ethyl group, an n-propyl group, an n-butyl group, an n-pentyl group, and an n-hexyl group. These three Rs are preferably the same from the standpoint of easy availability and purification after the reaction.

Examples of the orthoformate ester (2) include methyl orthoformate, ethyl orthoformate, propyl orthoformate, butyl orthoformate, pentyl orthoformate, and hexyl orthoformate. From the standpoint of easy availability, methyl orthoformate and ethyl orthoformate are preferable.

The amount of the orthoformate ester (2) to be used for the nucleophilic substitution reaction is preferably from 1.0 to 3.0 mol per mol of the (6Z,9Z)-1-halo-6,9-pentadecadiene (1-6Z9Z).

Examples of the solvent to be used for the nucleophilic substitution reaction include hydrocarbons such as toluene, xylene and hexane; and ethers such as tetrahydrofuran and diethyl ether. From the standpoint of reactivity, a mixed solvent of tetrahydrofuran and toluene is preferable. The amount of the solvent is preferably from 100 to 800 g per mol of the (6Z,9Z)-1-halo-6,9-pentadecadiene (1) from the standpoint of reactivity.

In the formula of (7Z,10Z)-1,1-dialkoxy-7,10-hexadecadiene (3), R has the same meaning as that of the orthoformate ester (2).

Examples of the (7Z,10Z)-1,1-dialkoxy-7,10-hexadecadiene include (7Z,10Z)-1,1-dimethoxy-7,10-hexadecadiene, (7Z,10Z)-1,1-diethoxy-7,10-hexadecadiene, and (7Z,10Z)-1,1-dipropoxy-7,10-hexadecadiene.

The reaction temperature for the nucleophilic substitution reaction is preferably from 75 to 130° C. from the standpoint of allowing the reaction to proceed smoothly and preventing evaporation of the solvent.

The reaction time for the nucleophilic substitution reaction is preferably from 3 to 35 hours, though it differs depending on the solvent used or a reaction scale.

Next, a method for producing (7Z,10Z)-7,10-hexadecadienal (9) will be described.

The (7Z,10Z)-7,10-hexadecadienal of Formula (9) below may be produced by a hydrolysis reaction of the (7Z,10Z)-1,1-dialkoxy-7,10-hexadecadiene (3). The hydrolysis reaction can be carried out, for example, by treating the (7Z,10Z)-1,1-diethoxy-7,10-hexadecadiene (3) with water and an acid in a solvent.

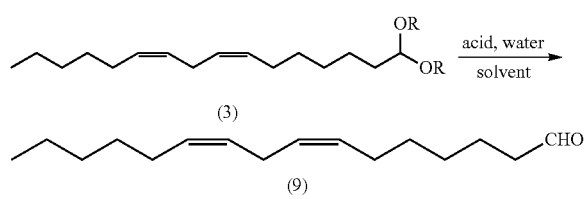

Examples of the acid to be used for the hydrolysis reaction include an inorganic acid such as hydrochloric acid and hydrobromic acid; p-toluenesulfonic acid; trifluoroacetic acid; acetic acid; formic acid; oxalic acid; iodo-trimethylsilane; and titanium tetrachloride. From the standpoint of reactivity, oxalic acid is preferable.

The amount of the acid to be used for the hydrolysis reaction is preferably from 0.01 to 10.0 mol per mol of the (7Z,10Z)-1,1-diethoxy-7,10-hexadecadiene (3).

Examples of the solvent to be used for the hydrolysis reaction include hydrocarbons such as toluene, xylene and hexane; ethers such as tetrahydrofuran and diethyl ether; polar solvents such as N,N-dimethylformamide, N,N-dimethylacetamide, acetonitrile, dichloromethane and chloroform; and alcohols such as methanol and ethanol. An optimum solvent is variable depending on the acid used. For example, when oxalic acid is used as the acid, tetrahydrofuran is preferable from the standpoint of reactivity. The amount of the solvent is preferably from 0 to 3000 g per mol of the (7Z,10Z)-1,1-diethoxy-7,10-hexadecadiene (3) from the standpoint of reactivity.

The amount of water to be used in the hydrolysis reaction is preferably from 18 to 3000 g per mol of the (7Z,10Z)-1,1-diethoxy-7,10-hexadecadiene (3) from the standpoint of reactivity.

The reaction temperature for the hydrolysis reaction is preferably from 5 to 150° C. from the standpoint of reactivity, though it differs depending on the solvent used.

The reaction time for the hydrolysis reaction is typically from 1 to 10 hours, though it differs depending on the solvent used or a reaction scale.

Thus, the 1-halo-6,9-pentadecadiene (1) useful as an intermediate having a skipped diene skeleton and the (7Z,10Z)-7,10 hexadecadienal (9), which is a sex pheromone of Chilean carpenter moth (*Chilecomadia valdiviana*), can be produced.

EXAMPLES

The invention will hereinafter be described in detail by Examples. It should not be construed that the invention is limited to or by Examples.

Example 1

Production No. 1 of (6Z,9Z)-1-chloro-6,9-pentadecadiene (1-6Z9Z)

Triphenylphosphine (165.24 g, 0.63 mol), sodium iodide (98.93 g, 0.66 mol), (3Z)-1-chloro-3-nonene (106.05 g, 0.63 mol) and acetonitrile (481.12 g) were placed in a reactor, and stirred under reflux conditions of from 75 to 85° C. for 13 hours. After stirring, the reaction product mixture was cooled to from 30 to 40° C. and tetrahydrofuran (865.36 g) was added thereto. Then, the resulting mixture was cooled to −60° C. and subjected to addition of potassium tert-butoxide (64.52 g, 0.58 mol). After stirring for one hour, 6-chlorohexanal (67.30 g, 0.50 mol) was dropwise added thereto over 30 minutes. After completion of the dropwise addition, the reaction product mixture was stirred for 30 minutes, then the temperature thereof was increased to 20° C. and the reaction was terminated. Pure water (1000 g) and salt (100 g) were added thereto to separate the reaction product mixture. The organic phase was concentrated under reduced pressure, and the residue was distilled under reduced pressure to obtain (6Z,9Z)-1-chloro-6,9-pentadecadiene (1-6Z9Z) (105.55 g, 0.43 mol, 6Z9Z/6E9Z=97.3/2.7) in a yield of 86.9%.

(6Z,9Z)-1-Chloro-6,9-pentadecadiene (1-6Z9Z)

[Nuclear magnetic resonance spectrum] $^1$H-NMR (500 MHz, CDCl$_3$): δ=0.89 (3H, t, J=7.3 Hz), 1.24-1.49 (10H, m), 1.78 (2H, tt, J=6.9, 6.9), 2.07 (4H, dt, J=7.3, 13.2 Hz), 2.78 (2H, dd, J=6.5 Hz), 3.53 (2H, t, J=6.5 Hz), 5.29-5.43 (4H, m); $^{13}$C-NMR (125 MHz, CDCl$_3$): δ=14.04, 22.56, 25.62, 26.52, 27.00, 27.19, 28.89, 29.32, 31.51, 32.53, 45.01, 127.75, 128.41, 129.54, 130.28

[Mass spectrum] EI-mass spectrum (70 eV): m/z 242 (M$^+$), 158, 123, 109, 95, 81, 67, 54

[Infrared absorption spectrum] (NaCl): ν=2956, 2928, 2857, 1461, 727

Example 2

Production No. 2 of (6Z,9Z)-1-chloro-6,9-pentadecadiene (1-6Z9Z)

Triphenylphosphine (165.24 g, 0.63 mol), sodium iodide (98.93 g, 0.66 mol), (3Z)-1-chloro-3-nonene (106.05 g, 0.63 mol) and acetonitrile (481.12 g) were placed in a reactor, and stirred under reflux conditions of from 75 to 85° C. for 16 hours. After stirring, the reaction product mixture was cooled to from 30 to 40° C. and tetrahydrofuran (865.36 g) was added thereto. The resulting mixture was then cooled to −5° C. and subjected to addition of sodium ethoxide (32.36 g, 0.58 mol). After stirring for one hour, 6-chlorohexanal (47.51 g, 0.35 mol) was dropwise added thereto over 15 minutes. After completion of the dropwise addition, the reaction product mixture was stirred for 20 minutes, then the temperature was increased to 20° C. and the reaction was terminated. Pure water (1000 g) and salt (100 g) were added thereto to separate the reaction product mixture. The organic phase thus obtained was concentrated under reduced pressure, and the residue was distilled under reduced pressure to obtain (6Z,9Z)-1-chloro-6,9-pentadecadiene (1-6Z9Z) (65.83 g, 0.27 mol, 6Z9Z/6E9Z=98.8/1.2) in a yield of 76.8%.

Example 3

Production of (7Z,10Z)-1,1-diethoxy-7,10-hexadecadiene (3)

Magnesium (25.25 g, 1.04 mol) and tetrahydrofuran (283.41 g) were placed in a reactor, and stirred at from 60 to 65° C. After stirring, (6Z,9Z)-1-chloro-6,9-pentadecadiene (229.40 g, 0.94 mol, 6Z9Z/6E9Z=97.3/2.7) was dropwise added thereto at from 60 to 75° C., and stirred at from 75 to 80° C. for 2 hours to prepare a Grignard reagent.

Then, toluene (439.29 g) and ethyl orthoformate (182.01 g, 1.23 mol) were added to the reactor at from 75 to 85° C. and stirred at from 90 to 100° C. for 29 hours. After cooling to from 30 to 45° C., 20% by weight aqueous hydrogen chloride (130.80 g), water (141.70 g) and acetic acid (26.10 g) were added to the resulting reaction product mixture to separate the reaction product mixture. The organic phase thus obtained was concentrated under reduced pressure, and the residue was distilled under reduced pressure to obtain (7Z,10Z)-1,1-diethoxy-7,10-hexadecadiene (3) (210.68 g, 0.68 mol, 6Z9Z/6E9Z=97.3/2.7) in a yield of 71.8%.

(7Z,10Z)-1,1-Diethoxy-7,10-hexadecadiene (3)

[Nuclear magnetic resonance spectrum] $^1$H-NMR (500 MHz, CDCl$_3$): δ=0.88 (3H, t, J=7.3 Hz), 1.19 (6H, t, J=6.9 Hz), 1.22-1.40 (12H, m), 1.60 (2H, dt, J=8.6, 5.7 Hz), 2.04 (2H, dt, J=6.9, 6.9 Hz), 2.76 (2H, dd, J=6.5, 6.5 Hz), 3.48 (2H, dq, J=5.7, 6.9 Hz), 3.63 (2H, dq, J=5.7, 6.9 Hz), 4.47 (1H, t, J=5.7 Hz), 5.28-5.41 (4H, m); $^{13}$C-NMR (125 MHz, CDCl$_3$): δ=14.04, 15.33, 22.55, 24.63, 25.59, 27.12, 27.17, 29.12, 29.32, 29.56, 31.49, 33.54, 60.78, 102.90, 127.87, 128.05, 129.97, 130.18

[Mass spectrum] EI-mass spectrum (70 eV): m/z 309 (M$^+$−1), 265, 219, 103, 29

[Infrared absorption spectrum] (NaCl): ν=2974, 2928, 2857, 1458, 1374, 1128, 1062, 724

Example 4

Production of (7Z,10Z)-7,10-hexadecadienal (9)

(7Z,10Z)-1,1-diethoxy-7,10-hexadecadiene (189.38 g, 0.61 mol, 6Z9Z/6E9Z=97.3/2.7), oxalic dihydrate (230.67 g, 1.83 mol), tetrahydrofuran (609.9 g) and pure water (609.9 g) were placed in a reactor, and stirred at from 60 to 65° C. for 3 hours. After cooling to 50° C., hexane (179.37 g) was added thereto. The resulting mixture was stirred for 30 minutes, and then the reaction mixture was separated. The organic phase thus obtained was concentrated under reduced pressure, and the residue was distilled under reduced pressure to quantitatively obtain (7Z,10Z)-7,10-hexadecadienal (9) (145.47 g, 0.62 mol, 6Z9Z/6E9Z=98.0/2.0).

(7Z,10Z)-7,10-Hexadecadienal (9)

[Nuclear magnetic resonance spectrum] $^1$H-NMR (500 MHz, CDCl$_3$): δ=0.88 (3H, t, J=6.9 Hz), 1.23-1.43 (10H, m), 1.63 (2H, tt, J=7.4, 7.4 Hz), 2.04 (2H, dt, J=7.3, 7.3 Hz), 2.06 (2H, dt, J=6.9, 6.9 Hz), 2.42 (2H, dt, J=1.9, 7.4 Hz), 2.76 (2H, dd, J=6.1, 6.1 Hz), 5.28-5.41 (4H, m), 9.76 (1H, t, J=1.9 Hz); $^{13}$C-NMR (125 MHz, CDCl$_3$): δ=14.03, 21.94, 22.54, 25.59, 26.93, 27.17, 28.75, 29.30, 29.32, 31.48, 43.83, 127.75, 128.32, 129.59, 130.24, 202.67

[Mass spectrum] EI-mass spectrum (70 eV): m/z 236 (M$^+$), 207, 193, 179, 165, 151, 137, 123, 95, 81, 67, 55, 41

[Infrared absorption spectrum] (NaCl): ν=2955, 2928, 2857, 1728, 1462, 724

The invention claimed is:

1. A method for producing (7Z,10Z)-7,10-hexadecadienal of Formula (9):

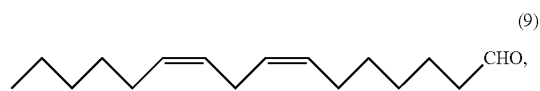

comprising steps of:
subjecting a Grignard reagent formed from a (6Z,9Z)-1-halo-6,9-pentadecadiene of Formula (1-6Z9Z):

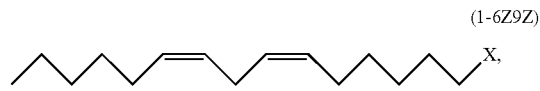

wherein X stands for a halogen atom,
to a nucleophilic substitution reaction with an orthoformate ester of Formula (2):

wherein R may be same with or different from each other and stands for an alkyl group having from 1 to 6 carbon atoms,
to obtain a (7Z,10Z)-1,1-dialkoxy-7,10-hexadecadiene of Formula (3):

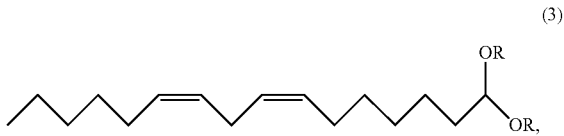

wherein R may be same with or different from each other and stands for an alkyl group having from 1 to 6 carbon atoms; and
hydrolyzing the (7Z,10Z)-1,1-dialkoxy-7,10-hexadecadiene (3) to obtain the (7Z,10Z)-7,10-hexadecadienal (9).

2. The method for producing (7Z,10Z)-7,10-hexadecadienal according to claim 1, further comprising steps of:
subjecting a triarylphosphonium (3Z)-3-nonylide of Formula (4-3Z):

wherein Ar may be same with or different from each other and stands for an aryl group,
to a Wittig reaction with a 6-halohexanal of Formula (5):

OHC(CH$_2$)$_5$X     (5), wherein X stands for a halogen atom,
to obtain the (6Z,9Z)-1-halo-6,9-pentadecadiene (1-6Z9Z), and
converting the (6Z,9Z)-1-halo-6,9-pentadecadiene (1-6Z9Z) into the Grignard reagent.

3. The method for producing (7Z,10Z)-7,10-hexadecadienal according to claim 2, further comprising a step of treating a 3-nonyltriarylphosphonium halide with a metal alkoxide of an alcohol having a pKa of from 12.0 to 16.5 at a temperature of from −20 to 0° C. to obtain the triarylphosphonium (3Z)-3-nonylide (4-3Z).

4. A 1-halo-6,9-pentadecadiene of Formula (1):

CH$_3$(CH$_2$)$_4$CH=CHCH$_2$CH=CH(CH$_2$)$_5$X     (1), wherein X stands for a halogen atom.

5. A method for producing a (6Z,9Z)-1-halo-6,9-pentadecadiene of Formula (1-6Z9Z):

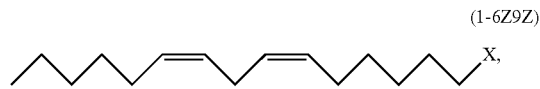

(1-6Z9Z)

comprising a step of subjecting a triarylphosphonium (3Z)-3-nonylide of Formula (4-3Z):

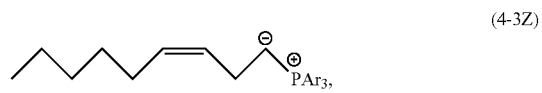

(4-3Z)

wherein Ar may be same with or different from each other and stands for an aryl group, to a Wittig reaction with a 6-halohexanal of Formula (5):

OHC(CH$_2$)$_5$X     (5), wherein X stands for a halogen atom, to obtain the (6Z,9Z)-1-halo-6,9-pentadecadiene (1-6Z9Z).

6. The method for producing a (6Z,9Z)-1-halo-6,9-pentadecadiene according to claim 5, further comprising a step of treating a 3-nonyltriarylphosphonium halide with a metal alkoxide of an alcohol having a pKa of from 12.0 to 16.5 at a temperature of from −20 to 0° C. to obtain the triarylphosphonium (3Z)-3-nonylide (4-3Z).

\* \* \* \* \*